(12) United States Patent
Steinemann

(10) Patent No.: US 8,168,012 B2
(45) Date of Patent: May 1, 2012

(54) BINARY TITANIUM-ZIRCONIUM ALLOY FOR SURGICAL IMPLANTS AND A SUITABLE MANUFACTURING PROCESS

(75) Inventor: Samuel Steinemann, Saint-Sulpice (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 12/367,978

(22) Filed: Feb. 9, 2009

(65) Prior Publication Data

US 2009/0139617 A1    Jun. 4, 2009

Related U.S. Application Data

(63) Continuation of application No. 10/750,446, filed on Dec. 31, 2003, now abandoned, which is a continuation of application No. 09/445,675, filed as application No. PCT/CH97/00230 on Oct. 6, 1997, now abandoned.

(51) Int. Cl.
*C22C 14/00* (2006.01)
*C22F 1/18* (2006.01)

(52) U.S. Cl. .................. 148/421; 420/417; 148/670

(58) Field of Classification Search .......... 420/417–421; 148/421, 670
See application file for complete search history.

(56) References Cited

U.S. PATENT DOCUMENTS

| 4,857,269 A | 8/1989 | Wang et al. |
| 5,169,597 A | 12/1992 | Davidson et al. |
| 5,820,707 A | 10/1998 | Armick et al. |

FOREIGN PATENT DOCUMENTS

| CH | 544154 | 7/1970 |
| GB | 1305879 | 2/1973 |

OTHER PUBLICATIONS

Chemical Abstracts, vol. 119, No. 10 (1993).
Database Metadex Materials Information, the Institute of Metals, London GB, Amick, (University of Idaho), abstract of "An Investigation of Reaction Forming by Controlled Passivation of Titanium-Zirconium Alloys with Niobium" (1994).
Massalski, T.B., "Binary Alloy Phase Diagrams Vo. 2", American Society for Metals, Ohio, pp. 2142-2143 (1986).
"Effect of Alloying Elements on Mechanical Properties of Titanium Alloys for Medical Implants", J. Japan Inst. Metals, vol. 57, No. 3 (1993) pp. 332-337.

*Primary Examiner* — Roy King
*Assistant Examiner* — Janelle Morillo
(74) *Attorney, Agent, or Firm* — Wenderoth, Lind, Ponack, L.L.P.

(57) ABSTRACT

The present invention relates to a binary single phase titanium-zirconium alloy suitable for the production of surgical implants. The alloy includes a zirconium content of less than 25% but more than 5% by weight, and 0.1% to 0.3% by weight of oxygen as a strength enhancing additive, and not more than 1% by weight of other strength enhancing additives and technical impurities.

12 Claims, No Drawings

BINARY TITANIUM-ZIRCONIUM ALLOY FOR SURGICAL IMPLANTS AND A SUITABLE MANUFACTURING PROCESS

CROSS-REFERENCE TO RELATED APPLICATIONS

This application is a continuation of application Ser. No. 10/750,446, filed Dec. 31, 2003, abandoned, which is a continuation of application Ser. No. 09/445,675, filed Sep. 13, 2000, abandoned, which is a §371 of PCT/CH97/00230 filed on Oct. 6, 1997, the contents all of which are incorporated hereby by reference.

FIELD OF THE INVENTION

The present invention relates to an alloy of titanium (Ti) and zirconium (Zr) for the production of surgical implants. A first application includes, for example, screws, plates and pins for fracture treatment and surgical orthopedics as well as endoprostheses. A second application includes dental surgery with in-bone implants, abutments and elements for suprastructures. The alloy is furthermore suitable for implants to anchor prostheses in the facial area, e.g. for maxillofacial and extraoral implants. The invention furthermore relates to a process for the production of such an alloy.

BACKGROUND OF THE INVENTION AND PRIOR ART

The metallic materials used today for surgical implants are:
stainless steel in accordance with international standard ISO-Norm 5832-1;
cobalt-chromium-molybdenum alloys in accordance with ISO 58324, 5832-5 and 5832-6;
unalloyed titanium in accordance with ISO 5832-2;
alloys: titanium-aluminum-vanadium (Ti6Al4V) in accordance with ISO 5832-3; titanium-aluminum-iron (Ti5Al2, 5Fe) in accordance with ISO 832-10; titanium-aluminum-niobium (Ti6Al7Nb) in accordance with ISO 5832-11.

"The ability of a material to perform with appropriate host response in a specific situation" (cf. D. F. Williams: in Biomaterials: Proceedings of a Consensus Conference of the European Society for Biomaterials. Elsevier Science Publ. Amsterdam, 1989). The foreign body produces only a minimal reaction in the living tissue. In the tissue in contact with the metal, sequestration in the form of encapsulation without pathological cell forms, or inertia, detectable as loose connective tissue, is observed (cf. S. G. Steinemann: Corrosion of Titanium and Titanium Alloys for Surgical Implants. Titanium, Science and Technology, Proc. 5th Int. Conf. Titanium. [G. Lütjering, U. Zwicker, W. Bunk, eds.], Deutsche Ges. Metallk. Oberursel, 1985, 1373).

For dental implants that are anchored in the bone, a higher form of tissue compatibility, namely osseointegration, is effective. In P.-I. Branemark, G. A. Zarb. T. Albrektsson [editors]: Tissue-Integrated Prostheses, Quintessenz Publ. Chicago, 1985, p. 11, we read: "Osseointegration is defined as a direct structural and functional connection between ordered, living bone and the surface of a load-carrying implant." This reaction implies an interaction between the foreign body and the living tissue, that is, more than just inert behavior of the metal. Dental implants are produced from titanium. For this metal, animal tests have shown complete anchoring, namely a rigid connection against the effects of pressure, shear and tension (cf. S. G. Steinemann, F. Straumann: [Ankylotische Verankerung von Implantaten] Ankylotic Anchoring of Implants. Schweiz. Mschr. Zahnmed. 94, 1984, 682). Complete anchoring also means adhesion, which is attributed to chemisorption (cf. S. G. Steinemann, J. Eulenberger, P.-A. Mäusli, A. Schroeder: Adhesion of Bone to Titanium. Biological and Biomechanical Performance of Biomaterials [P. Christel, A. Meunier, A J. C. Lee, eds.], Elsevier Sci. Publ. Amsterdam, 1986, 409).

Implants of bone and dental surgery are subject to high stresses and must be mechanically strong. Important parameters are yield point, elongation at break and modulus of elasticity. Stainless steel and unalloyed titanium have low strength and are therefore cold worked. For titanium, this increases the tensile strength from approximately 500 MPa to approximately 700 MPa. However, the strength of the two standard titanium alloys, which ranges from 900-1000 MPa, is not reached.

One experiment for measuring osseointegration is the implant expulsion test. For this purpose, a cylindrical implant is inserted into the bone in animal tests and the expulsion force is determined as a function of the rest period, typically 12 weeks. Such experiments have shown that the anchoring of mechanically roughened unalloyed titanium, Ti6Al4V and Ti6Al7Nb, is equal in strength but that a mechanically roughened and chemically etched surface for pure titanium implants results in much higher expulsion forces than an identical surface treatment for alloy implants (cf. M. Wong, J. Eulenberger, R. Schenk, E. Hunziker: Effect of surface topology on the osseointegration of implant materials in trabecular bone. J. Biomed. Mater. Res. 29, 1995, 1569). One or all of the three alloyed elements Al, V, Nb obviously inhibits integration in the bone.

Pure titanium and titanium alloys may exhibit local corrosion in narrow crevices if exposed to hot chloride-containing electrolytes. Manuals specify temperatures above 70° C. (cf. B. Craig: Technical Note Corrosion. in Material Properties Handbook: Titanium Alloys [R. Boyer, G. Welsch, E. W. Collings, eds.], ASM Int., Metals Park Ohio, 1994, 1065). However, there is clinical literature reporting corrosion in the crevice of cone connections of artificial hip joints and on the shaft of such prostheses in the cement bed. The known titanium materials for implants are obviously not resistant to crevice corrosion.

[Swiss Patent Application] CH-A-544 154 discloses a binary titanium-zirconium alloy with 25-75% by weight Zr for implants. The composition range corresponds to high mechanical strengths. These metals are reactive, exhibit exothermal oxidation and are therefore not easy to process. On the other hand, the alloy formula corresponds to an atom concentration of 15-61% Zr, i.e., the added element strongly influences electrochemical and biological reactions. This is not desirable and the reactions specific to titanium in the living tissue should not be lost.

OBJECT OF THE INVENTION

In view of the current lack of an optimal alloy for the aforementioned applications, the object of the invention is to create a metallic biomaterial which, firstly, exhibits high strength, secondly, is tolerated and integrated in both soft and hard tissue and, thirdly, is resistant to crevice corrosion.

SUMMARY OF THE INVENTION

A binary alloy of titanium and zirconium is proposed, wherein the added zirconium component is less than 25% by weight (14.9 atomic %) but more than 5% by weight (2.7 atomic %) resulting in a titanium-rich alloy. Preferred ranges of the zirconium content are between 19% by weight and 10% by weight.

The characteristics of the production process of the alloy are that the alloy is hot forged and subsequently cold worked. The forging process is carried out at temperatures above 850°

C. with subsequent rapid cooling of the alloy. Alternatively, the forging process may be carried out in the range of alpha/beta phase transition at 770° C. to 830° C. to produce special microstructures.

Thanks to the invention, a metallic biomaterial is now available for the defined field of application, which has sufficient strength as well as excellent tissue compatibility in soft and hard tissue and is moreover resistant to crevice corrosion.

DESCRIPTION OF DETAILS

It is known that the mechanical properties of titanium are substantially enhanced by adding zirconium (cf. A. G. Imgram, D. N. Williams, H. R. Ogden: Tensile properties of binary titanium-zirconium and titanium-hafnium alloys. J. Less-Common Metals 4, 1962, 217). Our own measurements on five alloys are given in Table 1. The alloys were melted from technically pure metals and, in addition to Ti and Zr, contained 0.09-0.11% O and 0.02-0.03% N; their condition was "forged above alpha-beta transition and cooled."

TABLE 1

| Composition % by wt. Zr | | Tensile Strength MPa | Yield Point MPa | Elongation at break % | Stress at break MPa |
|---|---|---|---|---|---|
| Ti | +5.1 | 496 | 429 | 23.1 | 1526 |
|    | +9.9 | 555 | 503 | 18.1 | 1436 |
|    | +14.9 | 655 | 559 | 14.5 | 1469 |
|    | +19.9 | 748 | 728 | 10.9 | 1454 |
|    | +25.6 | 779 | 670 | 8.5 | 1127 |

It is not generally known that the binary titanium-zirconium alloy can be further hardened by cold working and/or by adding oxygen. The alloys according to the invention are also readily cold worked, e.g., by rolling. The following strength values in accordance with Table 2 were measured on a Ti15Zr alloy that was annealed above the alpha-beta transition following hot forging:

TABLE 2

| Material Ti15Zr | Tensile strength MPa | Yield point MPa | Vickers Hardness kg/mm$^2$ |
|---|---|---|---|
| non cold worked | — | — | 203 |
| rolled 20% | 769 | 704 | 259 |
| 40% | 883 | 873 | 275 |
| 60% | 944 | 937 | 309 |

Oxygen must be considered a controlled alloy component that influences strength properties. Results are listed in Table 3.

TABLE 3

| Ti15Zr + Oxygen | Tensile strength [MPa] | Yield point [MPa] | Vickers Hardness [kg/mm$^2$] |
|---|---|---|---|
| 0.1% O | 655 | 559 | 203 |
| 0.2% O | 780 | 670 | 240 |
| 0.3% O | 864 | 735 | 267 |

The mechanical properties of the known titanium metals used today are shown in Table 4 (cf. ASM Metals Handbook 9$^{th}$ Edition, Vol. 3, Properties and Selection: Stainless Steels, Tool Materials and Special Purpose Metals. Amer. Soc. Metals, Metals Park Ohio, 1980, 353; S. G. Steinemann, P.-A. Mäusli, S. Szmukler-Moncler, M. Semlitsch, O. Pohler, H.-E. Hintermann, S. M. Perren: Beta-titanium alloy for surgical implants. Titanium 92 Science and Technology [F. H. Froes, I. Caplan, eds.], TMS Warrentale Pa., 1993, 2689).

TABLE 4

| Material | Tensile Strength MPa | Yield Point MPa | Elongation at break % | Stress at break MPa |
|---|---|---|---|---|
| Ti Grade 2 | 450 | | | |
| Grade 4 | 620 | 550 | 20.0 | |
| Grade 4 cold worked | 785 | 692 | 18.3 | 1095 |
| Ti6Al4V | 1076 | 940 | 14.7 | 1429 |
| Ti6Al7Nb | 1024 | 921 | 14.0 | 1400 |

The stress at break (load at break/cross section at point of break) is a measure for the toughness of a metal. It is remarkably high for single phase Ti—Zr alloys and approximately equal to that of two phase (alpha-beta) alloys Ti6Al4V and Ti6Al7Nb. Tensile strength and yield point of the material according to the invention are also better than those of cold worked unalloyed Grade 4 titanium and nearly reach those of the alpha-beta alloys if the effect of cold working and oxygen addition is used. Incidentally, cold working and the addition of oxygen do not change in any way the tissue compatibility of the binary Ti—Zr alloy.

Cell cultures are a common test for determining the reactions in the presence of metallic foreign bodies. For soft and hard tissue, experiments with fibroblast and osteoblast cells are of interest. Three such experiments were conducted. Firstly, growing osteoblasts on an inert plastic base with the metal oxides being dissolved in the culture medium (concentration approximately micromolar, saturated), secondly, growing fibroblasts on metal in the culture medium and, thirdly, growing osteoblasts on metal in the culture medium. The following reactions were observed (see Table 5):

TABLE 5

| Test | Retardation | No retardation |
|---|---|---|
| Osteoblasts in dissolved metal salt | | Al, Sn, Ti, Zr, Ta |
| Fibroblasts on metal | Cu, Mo, V | Ti, Nb, Zr, Ta |
| Osteoblasts on metal | Zn, Fe, Sn, Cu, Al, Mo, V, Ni, Ag, Nb, Ta | Ti, Zr |

No reaction of osteoblasts to the salts dissolved in the culture medium was found and the five metals tested also do not have a toxic effect in the implant test (see Steinemann, loc. cit., 1985). The result of the experiments with fibroblasts is the same as that of the implant test, where the four metals Ti, Nb, Zr and Ta exhibit inert behavior and Cu, Mo and V are toxic or cause sequestration. The result of the experiments with osteoblast cells that are in contact with the metal is clearly different; only Ti and Zr are inert. Growth of osteoblast cells and their unimpeded multiplication, however, is a prerequisite for both bone formation and osseointegration.

Adhesion of soft tissue and particularly also bone to the implant indicates a "bonding" reaction on an atomic scale between the organic and mineral materials and the metal. Organic materials are, for example, the amino acids as the building blocks of proteins and as the components of the so-called ground substance (organic component of bone). Calcium and phosphates are primary components of the bone mineral. One speaks of adsorption and chemisorption (short for chemical adsorption). It is known that amino acids are adsorbed to titanium oxide (anatase and rutile in powder form) and to zirconium oxide. It is also known that amino acids are chemisorbed to titanium metal oxidized in air (cf. J. M. Gold, M. Schmidt, S. G. Steinemann: XPS study of amino acid adsorption to titanium surfaces. Helv. Phys. Acta 62, 1989, 246; J. M. Gold, M. Schmidt, S. G. Steinemann: XPS study of retrieved titanium and Ti alloy implants. Clinical Implant Materials [G. Heimke, U. Soltesz, A. J. C. Lee, eds.], Elsevier Sci. Publ. Amsterdam, 1990, 69). It is not known whether and how amino acids are adsorbed to zirconium and Ti—Zr alloys and in what form calcium and phosphorus occur. Experiments by means of photoelectron spectroscopy provided the following results shown in Table 6.

TABLE 6

| Material | Amino acids | $Ca^{2+}$ | $H_2PO_4^-$ and $HPO_4^{2-}$ |
|---|---|---|---|
| Ti | ++ | ++ | ++ |
| Ti +25 wt.-% Zr | + | + | + |
| +50 wt.-% Zr | + | − | + |
| Zr | + | − | + |

Legend:
+ adsorbed
++ strongly adsorbed
− no adsorption

Amino acids are chemisorbed. Calcium and phosphate bind to the oxidized metal in the form of surface complexes. The reactions are strong, particularly for Ti rich alloys, and they involve all three reactants of osseointegration. On the other hand, adsorption is lacking or is weaker for zirconium rich alloys.

Alloying with Zr also has the advantageous effect that it increases the corrosion resistance of Ti in chloride-containing electrolytes. This effect enhances resistance to crevice corrosion, but only if the Zr content does not exceed 5% by weight.

The concentration of 25% by weight Zr corresponds to a particle concentration of 14.9 atomic % or 1 Zr atom to approximately 7 alloy atoms. This ratio characterizes the titanium rich alloy. If the proportion is 1 Zr/12 atoms in the metal, corresponding to 8.3 atomic % (=14.6% by weight), the alloy is said to be diluted and the titanium component then dominates with respect to the properties of the metal, particularly also with respect to compatibility and surface reactions. Thus, a preferred composition is the range of less than 19% by weight but more than 10% by weight zirconium. Particularly suitable for the purpose, then, is a metal with 14-15% by weight Zr.

This metal can be further hardened through cold working in accordance with the above figures. Strengths approaching 1000 MPa can then be reached, which approximates the properties of alpha-beta materials. The titanium alloy continues to include max. 0.30% by weight Fe, max. 0.05% by weight N, max. 0.10% by weight C and max. 0.015% by weight H as technical impurities. Depending on the production process (iodide or Kroll process), zirconium can contain 2-3% by weight hafnium, a non-toxic element. The alloy according to the invention may contain up to 0.5% by weight hafnium as impurity.

The invention claimed is:
1. A binary single phase titanium-zirconium alloy suitable for the production of surgical implants, said alloy comprising a zirconium content of 9.9% by weight to 19.9% by weight, 0.1% to 0.3% by weight of oxygen as a strength enhancing additive and not more than 1% by weight of other strength enhancing additives and technical impurities, the alloy being obtainable by a process involving the following steps:
  (i) hot forging said alloy at a temperature above alpha/beta phase transition; and
  (ii) rapidly cooling said alloy to obtain the single phase titanium-zirconium alloy;
  wherein said alloy is subsequently cold processed.
2. Titanium-zirconium alloy as claimed in claim 1, wherein the zirconium content is 14-15% by weight.
3. A device selected from the group consisting of implants in dental surgery, abutments and elements for suprastructures comprising the titanium-zirconium alloy of claim 1.
4. A process for producing a surgical implant, said process comprising incorporating into said implant a binary single phase titanium-zirconium alloy, said alloy comprising a zirconium content of 9.9% by weight to 19.9% by weight, 0.1% to 0.3% by weight of oxygen as a strength enhancing additive and not more than 1% by weight of other strength enhancing additives and technical impurities, the alloy being obtainable by a process involving the following steps:
  (i) hot forging said alloy at a temperature above alpha/beta phase transition; and
  (ii) rapidly cooling said alloy to obtain the single phase titanium-zirconium alloy;
  wherein the forging process is carried out at temperatures above 850° C., the alloy is then cooled rapidly and subsequently cold worked.
5. A surgical implant comprising the titanium-zirconium alloy of claim 1.
6. An implant for dental surgery, abutments and elements for suprastructures as in claim 5.
7. The titanium-zirconium alloy as in claim 1, wherein the alloy is hot forged and/or cold worked prior to processing into an implant.
8. A process for producing a surgical implant, said process comprising incorporating into said implant a binary single phase titanium-zirconium alloy, said alloy comprising a zirconium content of 9.9% by weight to 19.9% by weight, 0.1% to 0.3% by weight of oxygen as a strength enhancing additive and not more than 1% by weight of other strength enhancing additives and technical impurities, said process comprising:
  (a) forging the alloy in the range of alpha/beta phase transition at 770° C. to 830° C.;
  (b) cooling the alloy rapidly; and
  (c) cold working the alloy.
9. The titanium-zirconium alloy as in claim 1, comprising up to 0.5% by weight of hafnium as part of said technical impurities.
10. A surgical implant comprising a binary single phase titanium-zirconium alloy, said alloy comprising a zirconium content of 9.9% by weight to 19.9% by weight, 0.1% to 0.3% by weight of oxygen as a strength enhancing additive and not more than 1% by weight of other strength enhancing additives and technical impurities, the alloy being obtainable by a process involving the following steps:
  (i) hot forging said alloy at a temperature above alpha/beta phase transition; and
  (ii) rapidly cooling said alloy to obtain the single phase titanium-zirconium alloy;
  wherein said alloy is subsequently cold processed.
11. The surgical implant according to claim 10, wherein the zirconium content is 14-15% by weight.
12. The binary single phase titanium-zirconium alloy according to claim 1, suitable for the production of surgical implants, said alloy comprising a zirconium content of 9.9% by weight to 19.9% by weight, 0.1% to 0.3% by weight of oxygen as a strength enhancing additive and not more than

1% by weight of other strength enhancing additives and technical impurities, the alloy being obtainable by a process involving the following steps:
(i) hot forging said alloy at a temperature above alpha/beta phase transition; and
(ii) rapidly cooling said alloy to obtain the single phase titanium-zirconium alloy;
wherein said alloy is subsequently cold processed-and has a tensile strength of at least 769 MPa.

* * * * *